US00PP36599P3

(12) United States Plant Patent
Hansen

(10) Patent No.: US PP36,599 P3
(45) Date of Patent: Apr. 15, 2025

(54) ***PHLOX* PLANT NAMED 'Fancy Girl'**

(50) Latin Name: *Phlox paniculata*
Varietal Denomination: Fancy Girl

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 141 days.

(21) Appl. No.: 18/445,351

(22) Filed: Jul. 25, 2023

(65) Prior Publication Data

US 2025/0040458 P1 Jan. 30, 2025

(51) Int. Cl.
*A01H 5/02* (2018.01)
*A01H 6/70* (2018.01)

(52) U.S. Cl.
USPC ..... Plt./320
CPC ..... *A01H 6/70* (2018.05); *A01H 5/02* (2013.01)

(58) Field of Classification Search
USPC ..... Plt./320
See application file for complete search history.

*Primary Examiner* — Susan McCormick Ewoldt

(57) ABSTRACT

A new and unique hybrid cultivar of *Phlox* plant named 'Fancy Girl' of medium-height, multi-stemmed, upright habit. Foliage is lanceolate, medium-green, with good powdery mildew resistance on stiff stems. The new plant has Soft pink flowers with darker pink star-shaped center and near-white halo that are produced on large heads of branched peduncles and nearly cover the top of the plant beginning mid-July and continuing and reblooming for about six weeks through late summer. 'Fancy Girl' is especially suitable as a potted plant, for the garden, for attracting hummingbirds and butterflies, and for cut flower arrangements.

2 Drawing Sheets

Botanical classification: *Phlox paniculata.*
Variety denomination: 'Fancy Girl'.

STATEMENT REGARDING PRIOR DISCLOSURES UNDER 37 CFR 1.77(B)(6)

The first offer for sale of *Phlox* 'Fancy Girl' was on Jul. 28, 2022, and the first sale was by Walters Gardens, Inc. on Jul. 10, 2023. Walters Gardens, Inc. published an advertisement in their "Walters Gardens 13-24 Catalog" on Jun. 9, 2023. Walters Gardens, Inc. obtained the new plant and all information relating thereto, from the inventor. No plants of *Phlox* 'Fancy Girl' have been sold, or offered for sale in this country or anywhere in the world, under this or any name, nor has any disclosure of the new plant been made more than one year prior to the filing date of this application, and such sale or disclosure within one year was either derived directly or indirectly from the inventor.

BACKGROUND OF THE INVENTION

The present invention relates to a new and distinct hybrid Tall *Phlox* plant known as *Phlox* 'Fancy Girl' and will be referred to hereafter by its cultivar name or the "new plant". The new plant was the result of a controlled pollination of the proprietary, unreleased, hybrid known only as 14-598-1 (not patented) as the female or seed parent and the proprietary, unreleased, hybrid known only as 14-592-5 (not patented) as the male or pollen parent. The cross was performed by the inventor on Jul. 6, 2017, in the greenhouses at a wholesale perennial nursery in Zeeland, Michigan, and the seed was collected in the autumn of 2017. During the trial process the new plant arising as a single seedling selection from the identified cross was identified by the breeder code 17-36-5. 'Fancy Girl' has been asexually propagated by tip and basal stem cuttings in the greenhouses at the same nursery in Zeeland, Michigan since 2018, as well as by shoot tip tissue culture. The unique characteristics of the new plant have been found to be reproducible and stable in successive generations of asexually propagated plants and the resultant plants have been found to be identical to the original selection.

BRIEF SUMMARY OF THE PLANT

*Phlox* 'Fancy Girl' is unique from its parents and all other Tall Garden *Phlox* or other hybrid *Phlox* known to the inventor. The closest comparison cultivars known to the inventor are 'Opalescence' U.S. Plant Pat. No. 33,295, 'Pixie Twinkle' (not patented), 'Swizzle' U.S. Plant Pat. No. 19,813, and 'Bright Eyes' (not patented).

'Opalescence' is taller in habit with light pink flowers, having dark pink eyes, without the near white halo, and the foliage is darker green. 'Pixie Twinkle' has a much shorter habit, smaller flower heads, less overlapping of the petals, and the flowers are soft pink with a bright pink eye. 'Swizzle' is much smaller in habit, the flower heads are smaller with less overlapping and the flower color is more light reddish pink with a dark reddish pink eye. 'Bright Eyes' has a taller habit, the petals are not as overlapping and the flower color is more light reddish pink with a dark reddish pink eye.

'Fancy Girl' differs from all other *phlox* known to the inventor in the following repeatedly observed traits in combination:

1. Medium height plants of upright habit, producing clean, medium-green, lanceolate leaves;
2. Showing good powdery mildew resistance;

3. Multiple stems produce large, branched mounds of flowers starting in mid-July for about six weeks;
4. Soft pink flowers with darker pink star-shaped center and near-white halo on strong stiff stems;
5. Flowers cover nearly the entire top of the plant;

BRIEF DESCRIPTION OF THE DRAWINGS

The photographs of the new plant demonstrate the unique traits of 'Fancy Girl' and the overall appearance of three-year-old plants grown in a full sun trial garden in Zeeland, Michigan. The colors are as accurate as reasonably possible with color reproductions. Variation in ambient light spectrum, source and direction may cause the appearance of minor variation in color.

DETAILED BOTANICAL DESCRIPTION

Figure 1:
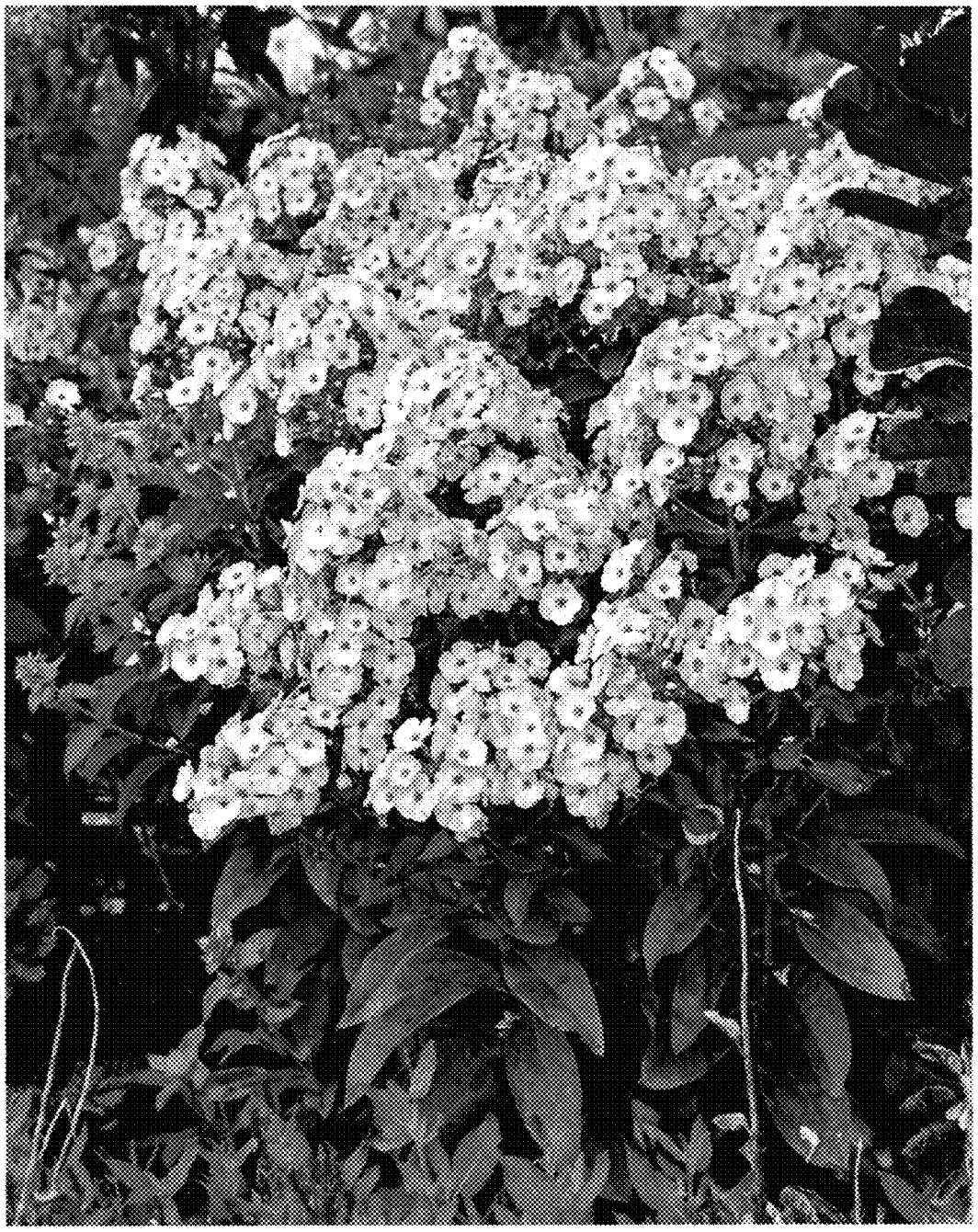
FIG. 1 shows the habit of the new plant in peak flower in the landscape.
Figure 2:
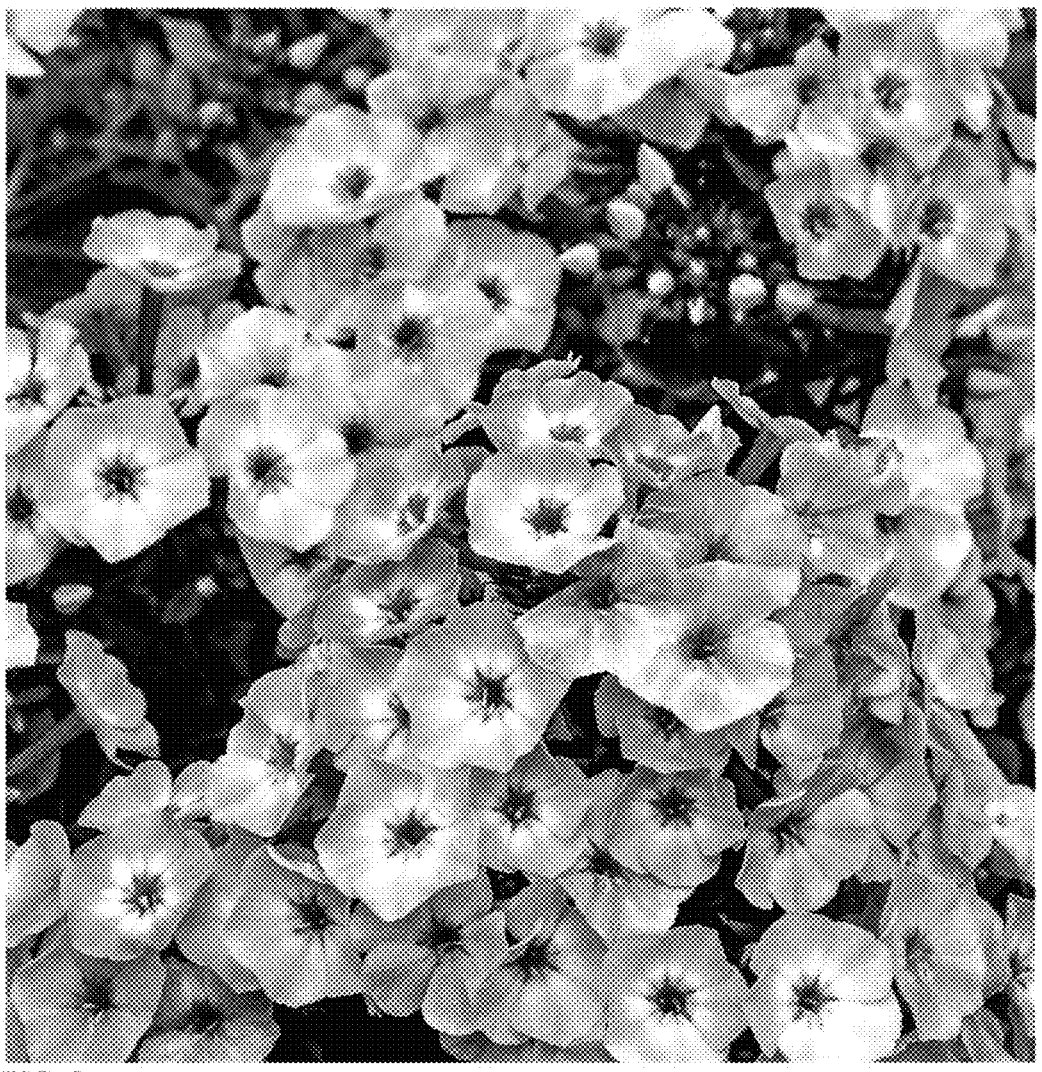
FIG. 2 shows a close-up of the floriferous flower head with flowers and buds.

The following descriptions and color references are based on the 2015 edition of The Royal Horticultural Society Colour Chart except where common dictionary terms are used. *Phlox* 'Fancy Girl' has not been observed in all possible environments. The phenotype may vary slightly with different growing environments such as temperature, light, fertility, soil pH, moisture, and maturity levels, but without any change in the genotype. The following observations and size descriptions are based on two-year-old plants in a partially-shaded greenhouse of a wholesale perennial nursery in Zeeland, Michigan with supplemental fertilizer and water as needed.

Botanical classification: *Phlox paniculata;*

Parentage: The proprietary, unreleased, hybrid known only as 14-598-1 as the female or seed parent, and the proprietary, unreleased, hybrid known only as 14-592-5 as the male or pollen parent;

Plant habit: Hardy herbaceous perennial, densely upright, producing about 8 rigid mostly upright stems; flowering at up to 75 cm tall and about 72 cm wide; flowering begins mid-July in Michigan and continuing for about 6 weeks with repeating into late summer;

Propagation: Stem cuttings; rooting in about 21 days;

Time to produce finished crop in 3.8-liter pots: About 10 to 12 weeks from a 25 mm liner; moderate rate of growth;

Root: Primary roots to about 1.0 mm thick; secondary fibrous and freely branching; color creamy white to tan depending on soil type; color of active roots nearest RHS NN155B depending on soil components;

Leaves: Simple; opposite; ovoid; acute apex; rounded to truncate base; sessile; micro-ciliolate margin; tough, coriaceous; glabrous adaxial and abaxial;

Leaf size: To about 12.5 cm long by about 6.4 cm wide; average about 10 cm long by about 5.2 cm wide; becoming smaller distally;

Leaf surfaces: Glabrous and lustrous adaxial, glabrous and matte abaxial;

Leaf color expanding: Adaxial between RHS 143A and RHS 146A, abaxial between RHS 147C and RHS 143C;

Leaf color at flowering: Adaxial between RHS NN137C and RHS 137A, abaxial nearest RHS 147B;

Foliage fragrance: None detected;

Veins: Pinnate; glabrous adaxial and abaxial; midrib about 1.5 mm wide at base, slightly sunken adaxial and raised abaxial;

Vein color: Adaxial midrib nearest RHS 146D and lateral veins between RHS 146B and RHS 146A, abaxial midrib nearest RHS 145C and lateral veins nearest RHS 146A;

Petiole: Leaves sessile;

Stems: About 8 per plant; cylindrical; stiff; wiry; strong; mostly upright; glabrous; to about 53 cm long below peduncle and 12 mm diameter at base, average about 48 cm long and 9 mm diameter at base;

Stem color: Nearest RHS 146C;

Nodes: About 14 per stem below initial flowers plus 15 nodes in branched flower head; average internode length about 2.6 cm;

Node color: Nearest RHS 146C;

Inflorescence: A branched compound corymb of about 150 flowers; flowering portion to about 28 cm long and 26 cm across;

Flowers: Perfect; salverform with flat face and long fused tube; actinomorphic; typically with five petals; about 24 mm long total with tube about 22 mm long and 2.5 mm diameter at base and 5 mm diameter below face; face about 30 mm across; attitude upright to slightly outward; self-cleaning;

Flower longevity: Individually about 5 days on plant or as cut flower;

Flower fragrance: Lightly sweet;

Buds one to two days prior to opening: Clavate; acute apex with petals convolute; base fused; total bud about 24 mm long, tube about 15 mm long and 2.5 mm diameter in tube base, bulb 9 mm long and swollen to 5 mm diameter toward apex;

Bud color: Petals nearest RHS 65D in bulb, and striated with a blend between RHS 71A and RHS 71B and nearest RHS 70C in distal corolla tube, proximal tube nearest RHS 145D;

Petals: Five; sympetalous; margin entire; apex rounded; base fused into tube; adaxial face and tube glabrous except proximal 5 mm of corolla tube pubescent, abaxial face glabrous and tube puberulent; limbs moderately imbricate, about 30 percent over the next petal;

Petal size: Limb to about 17 mm wide and about 12 mm long, corolla tube to about 22 mm long and 2.5 mm diameter at base and 5 mm diameter at face;

Petal color: Fading slightly with maturity; upon initial opening-adaxial limb distal portion nearest RHS N75C with center eye band about 2 mm wide between RHS N66C and RHS 67B and light halo between eye and main distal portion of nearest RHS 69B; upon initial opening — abaxial limb distal portion between RHS 77B and RHS 77C; at maturity — adaxial limb distal portion between RHS 69C and RHS 69B, with eye nearest RHS N74D having fine lines along midrib and petal margin of nearest RHS N74B, and halo between eye and distal portion nearest NN155D; at maturity — abaxial limb between RHS N155B and RHS NN155D; corolla tube not changing with maturity, adaxial corolla tube basal 5 mm nearest RHS 145D, distally between RHS 76A and RHS 78D; abaxial corolla tube basal 2.0 mm nearest RHS 155A, distally nearest RHS 77B; abaxial corolla tube basal 3 mm nearest RHS 145D and distally nearest RHS N75B;

Androecium: Five;

*Filaments.*—Typically, five; straight; cylindrical; adnate to adaxial corolla tube except free in distal 1 mm; varying lengths between 14 mm and 21 mm, about 0.2 mm in diameter; color between RHS N155B and RHS NN155D.

*Anther*.—Five; oblong elliptic; dorsifixed; longitudinal; about 3 mm long by 1 mm wide; color nearest RHS 11C.

*Pollen*.—Abundant; color nearest RHS 11D.

Gynoecium: One pistil per flower; to about 21 mm long;

*Style*.—Cylindrical; straight; about 18 mm long and about 0.3 mm diameter; persistent after flower abscission; color nearest RHS 145D transitioning to nearest RHS 182B after flower abscission.

*Stigma*.—Trifid in the distal 1 mm, about 0.3 mm in diameter; color nearest RHS 1D.

*Ovary*.—Superior; conical; acute apex, base truncate; about 2 mm long and 1 mm diameter; color nearest RHS 143A.

Calyx: Tubular; adpressed to corolla tube; to about 9 mm long and 3.5 mm cross at apex;

Sepals: Five; linear; narrowly acute apex, margin entire; basal 2 mm fused; adaxial surface glabrous and slightly lustrous, abaxial glabrous and slightly lustrous; persistent; individually about 9 mm long and 1 mm wide at fusion;

Sepal color: Adaxial nearest RHS 137C in center with translucent margins of nearest RHS 157D; abaxial nearest RHS 137C in center with moderate blush of nearest RHS 187A and translucent margins of nearest RHS 157D;

Peduncle: Glabrous, stiff, strong, moderately lustrous, upright, cylindrical; flowering portion average about 26 cm long, and 7 mm diameter at base of flower branches; branches to about 20 mm long and 3 mm diameter at base;

Peduncle color: RHS 146C;

Bracts: Subtending upper branches and flowers; lanceolate; ciliolate margin; acute apex; sessile truncate base; glabrous; to about 10 mm long and 4 mm wide;

Bract color: Same as leaves in both adaxial and abaxial surfaces;

Pedicel: Cylindrical; glabrous; to about 3 mm long and 1 mm diameter;

Pedicel color: Nearest RHS 146C;

Fruit: 1 or 2 seeded; dehiscent septicidal capsule; about 7.0 mm long and 4.5 mm across; acute apex; truncate base; color as nearest RHS 166B;

Seeds: Typically 1 to 2 per capsule; ellipsoidal; about 4.5 mm long×3.0 mm wide and 1.0 mm thick; color nearest a blend between RHS 200A and RHS 202A;

Hardiness and culture: The new plant grows best with plenty of moisture and adequate drainage; hardy to at least from USDA zone 4 through 8.

Disease and pest resistance: *Phlox* 'Fancy Girl' demonstrated the excellent powdery mildew resistance caused by *Erysiphe cichoracearum* in the presence and under conditions of intense pressure that would normally show symptoms.

I claim:

1. A new and distinct cultivar of hybrid *Phlox* plant named 'Fancy Girl', as herein described and illustrated.

* * * * *